United States Patent
Rau et al.

(10) Patent No.: US 10,022,318 B2
(45) Date of Patent: *Jul. 17, 2018

(54) EFFERVESCENT TABLETS/GRANULES

(71) Applicant: TOWER LAORATORIES, LTD, Centerbrook, CT (US)

(72) Inventors: Allen Rau, Cincinnati, OH (US); Nicole Quinn, Middletown, CT (US); Donald Stadolnik, Deep River, CT (US); Eric Sterner, Ivoryton, CT (US)

(73) Assignee: TOWER LABORATORIES, LTD., Centerbrook, CT (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/237,789

(22) Filed: Aug. 16, 2016

(65) Prior Publication Data

US 2016/0354306 A1 Dec. 8, 2016

Related U.S. Application Data

(63) Continuation of application No. 12/536,769, filed on Aug. 6, 2009, now Pat. No. 9,457,204.

(60) Provisional application No. 61/086,830, filed on Aug. 7, 2008.

(51) Int. Cl.
| | |
|---|---|
| *A61K 36/899* | (2006.01) |
| *A23L 2/395* | (2006.01) |
| *A23L 2/40* | (2006.01) |
| *A61K 8/19* | (2006.01) |
| *A61Q 19/10* | (2006.01) |
| *A61K 9/08* | (2006.01) |
| *C11D 3/10* | (2006.01) |
| *C11D 17/06* | (2006.01) |
| *A61K 9/46* | (2006.01) |
| *A61K 8/362* | (2006.01) |
| *A61K 9/16* | (2006.01) |
| *C11D 11/00* | (2006.01) |

(52) U.S. Cl.
CPC ............ *A61K 9/0007* (2013.01); *A23L 2/395* (2013.01); *A23L 2/40* (2013.01); *A61K 8/19* (2013.01); *A61K 8/362* (2013.01); *A61K 9/08* (2013.01); *A61K 9/1611* (2013.01); *A61K 9/1617* (2013.01); *A61K 36/899* (2013.01); *A61Q 19/10* (2013.01); *C11D 3/10* (2013.01); *C11D 11/0023* (2013.01); *C11D 17/06* (2013.01); *A23V 2002/00* (2013.01); *A61K 2800/222* (2013.01)

(58) Field of Classification Search
None
See application file for complete search history.

(56) References Cited

U.S. PATENT DOCUMENTS

| | | | | |
|---|---|---|---|---|
| 6,121,215 A | * | 9/2000 | Rau | A61K 8/0204 510/130 |
| 6,440,926 B1 | * | 8/2002 | Spadoni | A23L 2/40 510/276 |

FOREIGN PATENT DOCUMENTS

EP 0400858 * 12/1990

OTHER PUBLICATIONS

Ariel J. Raigrodski, Contemporary materials and technologies for all-ceramic fixed partial dentures: A review of the literature, The Journal of Prosthetic Dentistry, vol. 92, No. 6, pp. 557-561, Dec. 2004.*

* cited by examiner

*Primary Examiner* — Abigail Vanhorn
*Assistant Examiner* — Sarah J Chickos
(74) *Attorney, Agent, or Firm* — Steven B. Kelber; The Kelber Law Group

(57) ABSTRACT

This invention provides an effervescent solid form that dissolves in cold water quickly enough to not disappoint consumers yet not so quickly that the visual interest generated during the effervescent reaction is lost. This performance is achieved by forming effervescent particles that are dense enough to retard dissolution and small enough to not take too long to dissolve. The aim of this invention is to provide a beverage in solid effervescent form that takes between about 30 and about 120 seconds to dissolve in warm water. The granules may carry functional additives such as flavors, vitamins, minerals, sweeteners, colors and drugs. The granules may also be compounded of materials intended to provide relief from skin or topical discomfort, as in the form of a wash or bath additive. The granules may also be formulated to provide cleaning agents, such as ceramic cleaners and denture cleaners.

6 Claims, No Drawings

EFFERVESCENT TABLETS/GRANULES

PRIORITY DATA AND INCORPORATION BY REFERENCE

This application is a continuation of application Ser. No. 12/536,769, filed Aug. 6, 2009, allowed, which application claims benefit of priority to U.S. Provisional Patent Application No. 61/086,830 filed Aug. 7, 2008 which is incorporated by reference in its entirety.

BACKGROUND OF THE INVENTION

Field of the Invention

The present invention relates to mini-tablets or granules from which effervescent beverages, bath water and liquid formulations of various types can be prepared. The mini-tablets or granules are prepared such that effervescence commences and finishes within desired time frames.

Related Art

The art of products that effervesce when introduced to water or aqueous liquids is a crowded one. Typically, anhydrous products are prepared which, when introduced into a body of water—whether it be a glass or bathtub or something in between, effervesce to release carbon dioxide, which may help disperse the functional materials prepared with the effervescent materials into the liquid environment. In many cases, effervescence is deliberately introduced to capture consumer interest. This type of effervescence is desirably controlled by the duration of the effervescence. In the environment of a cold beverage, less than about half a minute is too little, more than about 2 or 2.5 minutes and the consumer interest is waning. In other environments, shorter durations are preferred.

The duration of effervescence is also controlled, to some degree, by the temperature of the water. A variety of medications and palliatives are available where the water is provided and is warm or hot (near boiling). In such situations, speed of delivery is more critical, and effervescence may perform a functional role, in distribution of the functional elements of the composition, instead of, or as an aid to, mechanical mixing. Thus, in warm water, the duration of effervescence may run from about 10-90 seconds, and in hot water, from 5-45 seconds.

The anhydrous products are typically formulated as powders, granules or tablets, in increasing order in terms of time to dissolve. U.S. Pat. No. 5,948,439, Forman, is representative of this art. Forman is focused on the preparation of effervescent granules, which release their effervescence quickly, but not as fast or energetically as powders. Neither the duration of the effervescence release, nor the density of the granules prepared, are set forth. U.S. Pat. No. 5,110,603, Rau, explains in more detail how effervescence can be employed to distribute functional elements of a bath composition more thoroughly than purely mechanical mixing. The material of this patent is prepared as a tablet, but neither the size nor the density of the tablet—nor the duration of its effervescence, is set forth.

BACKGROUND OF THE TECHNOLOGY

Effervescent tablets are well known. They utilize the combination of an edible acid and a carbonate salt to generate carbon dioxide gas when placed in water. Frequently, the effervescent components will be compounded with functional ingredients—materials intended to provide the user of the beverage with some type of benefit. Among other things, effervescent tablets can be used to deliver drugs, dietary supplements, flavors and fragrances.

Effervescent tablets that form beverages upon dissolution in water have been formulated. These tablets generally weigh from 2 to 20 grams. A common problem faced by the manufacturer is that they take a long time to dissolve, particularly in cold water. The effervescent action exhibited by these tablets as they dissolve can be interesting to the consumer. However, when the tablet's dissolution time exceeds about 2.5-3 minutes, the consumer becomes dissatisfied.

In order to avoid the long dissolution time of tablets, products in granular and powder forms have been developed. These approaches have problems though. Granules effervesce very quickly and do not provide extended visual interest. Powders tend to float on the water's surface, and if added to bottled water, can cause the water to overflow the container. Further, powders dissolve even more quickly than granules.

SUMMARY OF THE INVENTION

The needs of the marketplace to provide an effervescent composition that effervesces for a desired amount of time, depending on the temperature of the water in which it is placed, is met by providing "mini-tablets" or granules of a density of about 1.1-1.6 g/cc, more preferably 1.3-1.6, either by direct formation, or by grinding of tablets prepared to the indicated density, and then selecting for a given size range through a sieving process. Preferably, the products of the invention exhibit effervescence over 30-120 seconds when placed in warm liquids.

DETAILED DESCRIPTION

It is advantageous to define several terms before describing the invention. It should be appreciated that the following definitions are used throughout this application. As noted, in general, the provision of effervescent compositions of various types is an established art, and has a well established nomenclature. In general, terms used herein are intended to be used in their ordinary and common meaning with the field of effervescent compositions.

An important parameter that impacts the persistence of effervescence, one of the prime characteristics of the products of this invention, is density. Density, in its simplest expression, is mass per unit volume. And that is the way it is used herein. Commonly, in the industry where particulate matter of low density is involved, a product is placed in a tared graduated cylinder—the volume is noted, and then the product is weighed. The volume used to calculate density is that from the cylinder (alternatively, it can be done by filling a cup with a known volume and weighing the mass). This is a density figure that wrongly states the true density because it is impacted by air spaces in the product. The mini-tabs and granules of this invention are in fact compositions of this type, where the volume or bulk density is impacted by the presence of airspaces or gaps in the product. Where the term density is used herein, it is used in the sense of true density, that is, actual mass per unit volume.

Another parameter that has a major impact on effervescence duration is the temperature of the liquid in which the effervescing composition is to be placed. Those of skill in the art will appreciate that temperature is a continuum—but to speak in terms of applications and methods, it is useful to divide the temperature range over which the effervescent high density granules (or "minitabs") of this invention find principal application into arbitrary ranges. Thus, for the purposes of this application, cold liquids are those at or below refrigerator temperature and above freezing—approximately 35-45° F. This is the temperature that many consumer beverages will be at when the products of this invention are added. Tap water is typically at a temperature of 45-60° F., and clearly, the products of this invention will find wide application at these temperatures. This temperature range is arbitrarily designated cool in this application. Warm water, for example, bathing or washing water, ranges from above cool to shy of boiling. Temperatures from about 60-150° F. are generally considered warm for the purposes of this invention. Many beverages, teas, therapeutics and he like, are served just below the boiling point. So, liquids where the compositions of this invention are introduced that exhibit a temperature of from 150-212° F. are generally designated hot.

As a general rule, the higher the temperature of the liquid into which the compositions of this invention are introduced, the faster (shorter duration) and more energetic the effervescence. Thus, a formulation exhibiting effervescence over a period of, e.g., 60 seconds in warm temperatures will exhibit a shorter period of effervescence in hot water, perhaps as little as 45 seconds, again, depending on the actual composition of the high density granules, and the composition of the liquid. By the same token, the same composition will have a longer effervescent period in cool liquids, and the longest period exhibited by the same composition in, say, the same liquid, water, would be in cold water. It is appropriate then, to pick one temperature range and designate a period of effervescence for that range, knowing that the effervescence will vary across temperature ranges. In general, a period of effervescence of from about 30-120 seconds in warm water is a feature of the high density granules or minitablets of this invention.

Solid products designed to be diluted in water to become beverages generally weigh between 2 and 20 grams. The size of a specific product will be determined by the amount of "functional" ingredients it is designed to deliver, Functional ingredients include flavors, vitamins, minerals, drugs (such as analgesics, antihistamines, antiinflammatories, decongestants, expectorants, anti-flatulants, cough suppressants, stimulants, and/or sleep aids), sweeteners (natural and/or artificial), and color. Pharmaceutical and over the counter formulations are prepared in the same fashion, depending on whether the functional ingredient(s) included require a prescription or not. By the same token, largely cosmetic formulations, such as mouthwashes, which may advantageously incorporate antimicrobial agents, whitening and bleaching agents and fluoride or other agents effective in the oral cavity may be prepared in the form of the granules of this invention. Naturally sweetened products tend to be larger as large amounts of sugars or sugar alcohols (sucrose, dextrose, fructose, xylitol, sorbitol) are needed to provide acceptable consumer taste. High intensity sweeteners (such as saccharin, acesulfame-K, aspartame, sucralose, neotame, stevia, and luo han guo) can be used to formulate smaller products as lower levels of these materials are needed to achieve acceptable taste.

Effervescent formulations provide many functional attributes to beverage products:

The generation of carbon dioxide gas helps disperse the product evenly in the drink's container (either a glass or a purchased water bottle).

The fizzing action is interesting to consumers.

The concentrated form of the product eliminates the need to transport water over great distances and minimizes the amount of packaging needed.

The anhydrous nature of the product provides an environment where materials that may he susceptible to hydrolysis can be stable.

Effervescent products are formulated by using edible acids in combination with carbonate salts. Typical acids include citric acid, malic acid, tartaric acid, ascorbic acid, fumaric acid, adipic acid and sodium hydrogen sulfate, Commonly used carbonates are sodium carbonate, sodium bicarbonate, potassium carbonate, potassium bicarbonate, magnesium carbonate and calcium carbonate. Individual acids and carbonate salts can be used singly or in combination.

The time an effervescent product takes to dissolve is affected by several factors. In addition to the environment in which it is used, key among these factors are: its form (tablet, granule or powder); its size and its density; its hardness and the formulation itself.

Effervescent powders dissolve very quickly, generally within a few seconds. They react immediately, generally on the surface of the water, sometimes splattering water out of the container. When added to a narrow necked commercial water bottle, effervescent powders can often cause the liquid to over flow out of the container. Powder products are generally produced by simply blending the component powder materials.

Like powders, most granular effervescent products dissolve very quickly, again generally in less than 20-30 seconds. Granular products are more difficult (and expensive) to manufacture than powder blends. Usually the acid and carbonate salt are physically "glued" together using an edible or pharmaceutically acceptable binder such as polyvinyl pyrolidone, polyvinyl alcohol or polyethylene glycol. These types of granules are made by processes generically known as "wet granulation". Solvents such as ethanol and/or isopropyl alcohol are often used to aid this type of granulation process. These materials need to be removed from the granules, adding to the cost of production. Since the effervescent acid/carbonate couple is physically bound together in the granule, the gas generating reaction is usually quite vigorous, leading to the rapid dissolution times mentioned above. This performance can be seen with products like Bromo Seltzer™ and Brioschi™. Granules made by wet granulation techniques tend have low densities, typically less than 1 gm/cc.

Another type of "wet granulation" product that is specific to effervescent products is known as "fusion" type granules. These granules are formed by reacting the acid and carbonate materials with a small amount of water (or sometimes a hydrous alcohol, such as various commercial grades of ethanol or isopropyl alcohol) in a highly controlled way. Since the effervescent reaction generates carbon dioxide, fusion granules tend to be quite porous. This decreases their density and also their dissolution time.

Tablet formulations always dissolve more slowly than powders or granules. This is almost certainly due to their relatively large size, low porosity and high density. The presence of lubricants in tablet formulations (required for efficient processing) also, in general, hinders dissolution. Representative lubricants include polyethylene glycol, sodium benzoate, magnesium stearate, stearic acid, vegetable oil, various silicone polymers, sodium stearoyl fumarate, leucine, and ethoxylated fatty alcohols. Many of these materials tend to be hydrophobic and therefore can impede the water needed for effervescent reaction to take place, delaying or extending effervescence Effervescent tablets that are intended to become beverages are particularly difficult to formulate for rapid dissolution. This is may, at least in part, be due to the relatively high level of flavor oils needed to achieve consumer acceptability. As with the lubricants discussed above, it is reasonable to assume that the hydrophobic nature of most flavor oils inhibits the reaction of the acid and carbonate salts, thus slowing the effervescence. This hypothesis is supported by the fact that unflavored effervescent tablets dissolve much more quickly than flavored products.

Attempts to formulate effervescent beverage tablets have resulted in products that take at least 2.5 minutes to dissolve in cold (40° F.) water. It is not uncommon for even relatively small (2-3 gram) tablets to take over 3 minutes to dissolve. This is too long for consumers who want to partake of their beverage essentially immediately.

Many attempts to speed the dissolution time of effervescent tablets have been made. These efforts have focused on using more soluble carbonate salts (using potassium bicarbonate in place of sodium bicarbonate); increasing the ratio of acid to carbonate in order to drive the reaction more vigorously; and adding wicking materials (such as microcrystalline cellulose and/or soy polysaccharides) to help bring water into contact with the reactants more rapidly. Efforts to use these approaches continue and may someday be successful.

The most successful approach that we have found for reducing the dissolution time of an effervescent beverage tablet is to produce very small tablets ("mini-tablets") or dense granules that can be packaged together as a single serving.

In the examples below, small sphere shaped tablets, approximately 4.5 mm in diameter were compressed on a conventional tablet press. The appropriate total weight of the resulting tablets, which individually weighed approximately 65 mg each, were packaged in individual pouches as single servings. Clearly, the total amount of material in a given limited liquid may influence the period of effervescence as well. As an arbitrary standard for determining the period of effervescence, 5 grams of the high density material of this invention, of 1.1-1.6 g/cc, are placed in 150 ml of warm water. The dissolution period should range from 30-120 seconds.

As an alternate way of producing high density effervescent granules, we also produced large tablets and then broke and sieved them such that we could control their particle size. This can be accomplished by grinding the tablets using a cone (or other suitable) mill and then screening the resulting particles to the desired size. Particles that are too small can be re-compressed and run through this process multiple times. A key advantage of this production method is that it yields particles that have the same inherent density as the tablet originally pressed.

Following the above approach, granules were formed by coarsely grinding tablets to various sizes (6-10 mesh and 10-14 mesh) and were packaged as single servings. The typical weight of the larger (6-10 mesh granules was about 156 mg. The weight of the smaller (10-14 mesh) granules average about 37 mg.

For comparison purposes, single tablets (with weight equal to the total weight in the pouch) of the same composition were also produced. Data illustrating the findings follows.

Beverage tablet products were formulated with the following compositions:

|  | Lemon/Lime Drink | | Peach Tea Drink | | Herbal Energy Drink | |
| --- | --- | --- | --- | --- | --- | --- |
| Material | mg/serving | % w/w | mg/serving | % w/w | mg/serving | % w/w |
| Citric Acid | 1250 | 31.54 | 2400 | 42.22 | 2500 | 50.00 |
| Malic Acid | 255 | 6.43 | | | | |
| Potassium Bicarbonate | 154 | 3.87 | 808 | 14.22 | 253 | 5.06 |
| Sodium Bicarbonate | 634 | 16.00 | 808 | 14.22 | 775 | 15.50 |
| PEG 180 | 100 | 2.52 | 130 | 2.29 | 89 | 1.78 |
| Sodium Benzoate | 90 | 2.27 | 130 | 2.29 | 50 | 1.00 |
| Sorbitol | 198 | 5.00 | 600 | 10.56 | | |
| Black Tea Solids | | | 600 | 10.56 | | |
| Vitamin Blend | | | | | 353 | 7.06 |
| Herbal Blend | | | | | 160 | 3.20 |
| Caffeine | | | | | 75 | 1.50 |
| Microcrystalline Cellulose | | | | | 200 | 4.00 |
| Corn Syrup Solids | | | | | 237 | 4.74 |
| Sucralose | | | | | 17 | 0.34 |
| Aspartame | 47 | 1.18 | 126 | 2.23 | | 0 |
| Acesulfame-K | 17 | 0.43 | 54 | 0.93 | 40 | 0.80 |
| Flavor Solids | 1105 | 27.88 | | | 250 | 5.00 |
| Flavor Oil | | | 28 | 0.49 | | |
| Sodium Chloride | 82 | 2.06 | | | | |
| Magnesium Sulfate | 30 | 0.76 | | | | |
| Color | 2 | 0.06 | | | 1 | 0.02 |
| Total | 3964 | 100.00 | 5684 | 100.00 | 5000 | 100.00 |

Each formula was pressed to form both a single tablet (⅞" diameter) and to form mini-tablets (described above) using conventional pharmaceutical tablet presses. The compression force was adjusted so that non-capped/laminated tablets with hardness sufficient to withstand packaging and shipment. The granular product forms were produced by taking the single tablets and grinding them to the indicated mesh sizes. Dissolution time was determined by placing the single tablet or the equivalent weight of mini-tablets or granules in cold water.

Data are:

|  | Lemon/Lime Drink | Peach Tea Drink | Herbal Energy Drink |
|---|---|---|---|
| Single tablet | 6 min 7 sec | 2 min 28 sec | 3 min 35 sec |
| Mini-tablets | 2 min 40 sec | 1 min 23 sec | 1 min 41 sec |
| Large granules (6-10 mesh) | 58 sec | 49 sec | 1 min 9 sec |
| Small granules (10-14 mesh) | 35 sec | 27 sec | 51 sec |

These mini-tablets are different from comparably sized conventional granules of the prior art in that they are much denser. Typical tablet formulations have densities in the range of 1.3-1.6 grams/cc. in fact, the density of the 65 mg mini-tablets can be calculated at 1.36 gm/cc. As noted above, conventionally formed granules (formed without compression) have lower densities, typically 0.8-1.0 gm/cc.

Although the mini-tablets and granules described above were produced using a conventional tablet press, it is conceivable that comparable items can be formed using alternate processes. For instance, a roll compactor can be used to produce small, high density granules that would be comparable to those formed by grinding tablets. These granules will not dissolve instantaneously, yet would still go in to solution quite rapidly.

Although the intent of this invention is aimed at beverage products, it can easily be extended to other effervescent products. For instance, effervescent bath products can benefit from this product form. To illustrate this, an effervescent bath product was produced with the following formula:

| Material | mg/dose | % w/w |
|---|---|---|
| Colloidal Oatmeal | 793 | 1.98 |
| Fumaric Acid | 13888 | 34.72 |
| Sucrose Stearate | 5 | 0.01 |
| PEG-150 | 1314 | 3.29 |
| Soda Ash | 8000 | 20.00 |
| Sodium Bicarbonate | 8000 | 20.00 |
| Sorbitol | 3544 | 8.86 |
| Maltodextrin | 1600 | 4.00 |
| Silica | 200 | 0.50 |
| Botanical Extracts | 120 | 0.30 |
| Oat Oil | 320 | 0.80 |
| Oleth 10 | 200 | 0.50 |
| Fragrance | 400 | 1.00 |
| Titanium Dioxide | 1600 | 4.00 |
| Blue #1 | 16 | 0.04 |
| Total | 40,000.0 | 100.00 |

As with the beverage tablet products, this formulation was compressed into single tablet, mini-tablet and dense granule formats. Dissolution was measured in warm water (45° C.):

|  | Bath Product |
|---|---|
| Single tablet | 3 min 0 sec |
| Mini-tablets | 52 sec |
| Large granules (6-10 mesh) | 22 sec |
| Small granules (10-14 mesh) | 13 sec |

As can be seen, in the bath product, as with the beverage granules, an optimum dissolution time frame is achieved by providing an effervescent combination of acid and carbonate, and then functional additives (colloidal oatmeal, various extracts oils and fragrances, together with aesthetic additives (fragrance, colorants and the like) to arrive at a final composition that is then compounded into mini-tablets or high density granules exhibiting a density of about 1.3-1.6 g/cc and exhibit a sustained dissolution time frame within the "consumer interest" window of about 30-120 seconds, give or take 10%.

The choice of application, that is, the environment in which the granules of the invention are to be used and the purpose to which they are to be put will influence the selection of other ingredients selected to prepare the granules, whether by direct granulation, or tableting and grinding followed by sieving. Performance of the granules, and consumer acceptance of the resulting solution, may be improved by the addition of surfactants. In an environment where the granules and the liquid prepared by adding the granules to a base liquid is not to be ingested, such as in the case of a bath preparation, a wide range of surfactants can be employed. Surfactants may include, but are not limited to: sodium lauryl sulfate, sodium lauryl ethoxy sulfates, sodium lauryl sulfoacetate, sodium dodecyl benzene sulfonate, alpha olefin sulfonate, sodium lauryl sulfosuccinate, various fatty alcohols and fatty alcohol ethoxylates, and nonylphenol ethoxylates. In preparation of a beverage, surfactants are typically incorporated in flavors of various types. Examples include the various Tween™ surfactants, as well as lecithins.

The use environment may affect fundamental formulation. In the examples above, the granules of the invention have been described in terms of products that must be safe for animal (including human) use, either as a beverage or as a bath additive or solution for topical application. Many applications are not so constrained however. The granules of this invention lend themselves to preparation of cleaning agents, such as toilet bowl and sink cleaning agents (ceramic surface cleaners, generally). In this case, the functional ingredients are typically bleaches, such as sodium perborate, potassium monopersulfate (potassium caroate), sodium percarbonate, calcium percarbonate, urea peroxide and calcium peroxide. These are effectively combined with one or more of the surfactants set forth above to provide effective cleaning or bleaching solutions when dissolved in water or other work liquids. Of course, there are cleaning agents which although not intended for ingestion, must be at least non-poisonous, such as denture cleaners and the like, which are similarly prepared using the granules of this invention.

It will be appreciated that the effervescent materials (acid and carbonate), the active or functional ingredients (therapeutics such as oatmeal, aromas, pharmaceuticals and flavorants), formulation materials (e.g., lubricants such as those mentioned above and binders like maltodextrin, microcrystalline cellulose and sorbitol) and aesthetic ingredients (colorants and the like can be altered from those set forth in the examples above, and selected from those alternatives commonly used in the industry. Applicant's invention resides in the identification of products, and methods of making them, that give an active effervescence for the period identified as consumer preferred, by selecting a specific density and providing the same. These can be provided in the form of the compressed mini-tablets described above, as well as large and small granules described above. Those of skill in the art will appreciate that dissolution time for a beverage, where the consumer is watching the preparation, must be more closely controlled than other formulations, such as a bath product. By adjusting density within the specified range, the desired period of effervescence can be achieved.

While the present invention has been disclosed generically and with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. Granules which effervesce upon being combined with water, comprising an effervescent combination of an organic acid component and a carbonate salt component, said granules exhibiting a true density of from 1.3-1.6 g/cc, a particle size of approximately 6-14 mesh, and wherein said granules, when placed in water of 60-150° F., effervesce and completely dissolve over a period of 30-120 seconds, wherein said granules further comprise a functional component selected from the group consisting of bleaches.

2. The granules of claim 1, wherein said organic acid component is an acid selected from the group consisting of citric acid, malic acid, tartaric acid, ascorbic acid, fumaric acid, adipic acid, sodium hydrogen sulfate and mixtures thereof.

3. The granules of claim 1, wherein said carbonate salt component is a carbonate salt selected from the group consisting of sodium carbonate, sodium bicarbonate, potassium carbonate, potassium bicarbonate, magnesium carbonate, calcium carbonate and mixtures thereof.

4. A cleaning solution comprised of the granules of claim 1, wherein said granules are completely dissolved and wherein the functional component comprises bleach.

5. The cleaning solution of claim 4, wherein said cleaning solution comprises a ceramic surface cleaner.

6. The cleaning solution of claim 4, wherein said cleaning solution comprises a denture cleaner.

* * * * *